(12) United States Patent
Almhöjd et al.

(10) Patent No.: US 9,999,605 B2
(45) Date of Patent: Jun. 19, 2018

(54) PREPARATION FOR TREATMENT OF A NON-ORAL TREATMENT SITE COMPRISING AN ACTIVE CHLORINE COMPOUND AND AMINO ACIDS

(71) Applicant: RLS GLOBAL AB, Göteborg (SE)

(72) Inventors: Ulrica Almhöjd, Bohus-Björkö (SE); Karin Bergqvist, Bohus-Björkö (SE)

(73) Assignee: RLS Global AB, Göteborg (SE)

( * ) Notice: Subject to any disclaimer, the term of this patent is extended or adjusted under 35 U.S.C. 154(b) by 252 days.

(21) Appl. No.: 14/416,718

(22) PCT Filed: Jul. 15, 2013

(86) PCT No.: PCT/EP2013/064919
§ 371 (c)(1),
(2) Date: Jan. 23, 2015

(87) PCT Pub. No.: WO2014/016157
PCT Pub. Date: Jan. 30, 2014

(65) Prior Publication Data
US 2015/0174091 A1    Jun. 25, 2015

(30) Foreign Application Priority Data
Jul. 24, 2012 (SE) ....................... 1250891

(51) Int. Cl.
| | |
|---|---|
| A61K 31/198 | (2006.01) |
| A61K 47/02 | (2006.01) |
| A61K 47/38 | (2006.01) |
| A61K 33/20 | (2006.01) |
| A61K 31/59 | (2006.01) |
| A61K 45/06 | (2006.01) |

(52) U.S. Cl.
CPC ............ *A61K 31/198* (2013.01); *A61K 31/59* (2013.01); *A61K 33/20* (2013.01); *A61K 45/06* (2013.01); *A61K 47/02* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 3,950,536 A | 4/1976 | Barer et al. | |
| 7,879,798 B1 | 2/2011 | Aufseeser | |
| 9,314,017 B2 * | 4/2016 | Myntti | A01N 25/02 |
| 2003/0194445 A1 * | 10/2003 | Kuhner | A01N 37/46 424/622 |
| 2007/0032754 A1 * | 2/2007 | Walsh | A61M 27/00 602/2 |
| 2008/0319072 A1 * | 12/2008 | Torrence | A61K 31/198 514/562 |
| 2011/0282382 A1 * | 11/2011 | McAlister | A61B 17/00491 606/213 |

FOREIGN PATENT DOCUMENTS

| | | |
|---|---|---|
| AU | 2004268546 A1 | 3/2005 |
| AU | 2006208046 A1 | 8/2006 |
| AU | 2010281524 A1 | 2/2012 |
| AU | 2012241705 A1 | 10/2013 |
| GB | 1418193 A | 12/1975 |
| JP | S5030392 A | 3/1975 |
| JP | S56133213 A | 10/1981 |
| JP | S6081131 A | 5/1985 |
| JP | H10175857 A | 6/1998 |
| JP | 2001504818 A | 4/2001 |
| JP | 2007291115 A | 11/2007 |
| KR | 20080082742 A | 9/2008 |
| WO | WO-9820838 A1 | 5/1998 |
| WO | WO-9943344 A2 | 9/1999 |
| WO | WO-2002/002061 A2 | 1/2002 |
| WO | WO-2002/002063 A2 | 1/2002 |
| WO | WO-2002/058692 A2 | 8/2002 |
| WO | WO-2004/032979 A2 | 4/2004 |
| WO | WO-2006/081392 A1 | 8/2006 |
| WO | WO-2008/083347 A1 | 7/2008 |
| WO | WO-2008/137444 A1 | 11/2008 |
| WO | WO-2009/096993 A1 | 8/2009 |
| WO | WO-2010/017405 A1 | 2/2010 |
| WO | WO-2010/091280 A1 | 8/2010 |
| WO | WO-2010/0107807 A2 | 9/2010 |
| WO | WO-2011/014460 A1 | 2/2011 |
| WO | WO-2011/017030 A2 | 2/2011 |

(Continued)

OTHER PUBLICATIONS http://decubitusulcervictims.com/diabetic.ulcers.pressure.sores.*
PCT/EP2013/64919 (WO 2014/016157), Jul. 24, 2012, Almhöjd (RLS Global AB).
"CarisolvTM Sensitizing potential in the guinea-pig: Magnusson & Klingman test (G.P.M.T.)", Chrysalis, Preclinical services—Europe. a2PU1478, 1998, (1 page).
"CarisolvTM—Single application dermal irritation study in rat", Chrysalis, N 789/002-D-23, 1998, (pp. 1-32).
"CarisolvTM—Test to evaluate irritation of the buccal mucosa in the guinea-pig", Chrysalis, 789/001, 1998, (pp. 1-78).
"Silica fumed CarisolvTM—Acute Oral Toxicity Study in the Rat", OECD Guideline No. 420, Acute Oral Toxicity-fixed dose method, Bollen, ScanTox, lab 43241, DK, Jul. 2001, (pp. 1-15).

(Continued)

*Primary Examiner* — Robert A Wax
*Assistant Examiner* — Danah Al-Awadi
(74) *Attorney, Agent, or Firm* — Ballard Spahr LLP

(57) ABSTRACT

A kit of parts for use in prevention and/or treatment of a non-oral treatment site, such as, sores, wounds, ulcers or the like, or a fistula or otitis. The kit of parts comprises a first aqueous component comprising one or more amino acids, and a second aqueous component comprising an active halogen compound, wherein the pH of the first component and/or the second component is about 9 to 11.5. There is also provided a treatment preparation prepared from the components and uses thereof in the prevention and/or treatment of a non-oral treatment site, such as, sores, wounds, ulcers or the like, or a fistula or otitis.

38 Claims, 1 Drawing Sheet

(56) References Cited

FOREIGN PATENT DOCUMENTS

| WO | WO-2012/140272 A1 | 10/2012 |
|----|-------------------|---------|
| WO | WO-2014/016157 A1 | 1/2014  |

OTHER PUBLICATIONS

Armesto et al., "Alpha-Amino acids chlorination in aqueous media", Tetrahedron 1993, vol. 49, No. 1, (pp. 275-284).
Coetzee et al., "The Use of topical, un-buffered socium hypochlorite in the management of burn would infection", Jun. 2012, No. 4, 2012, (pp. 529-533).
Gottardi et al., "N-chlortaurine, a natural antiseptic with outstanding tolerability", Journal of Antimicrobial Chemotherapy, 2010, vol. 65, (pp. 399-409).
Greenwood et al., Chemistry of the Elements, 1985, (pp. 1000-1002).
Kaminiski et al., "N-Halo derivatives V:Comparative antimicrobial activity of soft N-chloramine systems", J. Pharm Sci 1976, vol. 65, No. 12, (pp. 1737-1742).
King et al., "Toxicological Evaluations of a Chemical Caries-Removing Agent" Preclinical Report, 1985, (pp. 1-6).
Leaper, "Eusol", BMJ, vol. 304, Apr. 11, 1992, (pp. 930-931).
Moore et al., "A systematic review of wound cleansing for pressure ulcers" J. Clinical. Nurs., 2008 17(15), (pp. 1963-1972).
Serena et al., "Consensus principles for wound care research obtained using Delphi process. Wound repair and regeneration", May 2012; 20(3), (pp. 284-293).
Tonami et al., "Effects of chloramines and sodium hypochlorite on carious dentin"; Journal of Medical and Dental Sciences, Jun. 2003, (pp. 139-146).
Weller et al., "Inorganic Chemistry", 6th Edition, Extract—Latimer diagrams, 2014, (p. 177).
Wikipedia Article, "Chrloramine," 2015, available at http://en.wikipedia.org/wiki/Chloramine, (10 pages).
Young et al., "A randomised, controlled and blinded histological and immunohistochemical investigation of Carisolv on pulp tissue" Journal of Dentistry, May 2001, (pp. 275-281).
International Search Report dated Oct. 9, 2013 for International Application PCT/EP2013/064919, which was filed on Jul. 15, 2013 and published as WO 2014/016157 on Jan. 30, 2014. (Inventor—Almhöld; Applicant—RLS Global AB. (pp. 1-59).
International Preliminary Report on Patentability dated Sep. 9, 2014 for International Application PCT/EP2013/064919, which was filed on Jul. 15, 2013 and published as WO 2014/016157 on Jan. 30, 2014. (Inventor—Almhöld; Applicant—RLS Global AB. (pp. 1-14).
Written Opinion of the International Searching Authority for International Application PCT/EP2013/064919, which was filed on Jul. 15, 2013 and published as WO 2014/016157 on Jan. 30, 2014. (Inventor—Almhöld; Applicant—RLS Global AB. (pp. 1-5).
Baker, R.W.R., Studies on the reaction between sodium hypochlorite and proteins; Biochem Journal, vol. 41; pp. 337-342 (1947).
Coetzee E, et al. The use of topical, un-buffered sodium hypochlorite in the management of burn wound infection, Burns 38(4):529-533(2012).
Gottardi et al., N-chloramines, a promising class of well-tolerated topical anti-infectives; Antimicrob. Agents Chemother. 57(3):1107 (2013).
Hawkins et al., Hypochlorite-induced oxidation of amino acids, peptides and proteins; Amino Acids 25, pp. 259-274, (2003).
Young et al, A randomised, controlled and blinded histological and immunohistochemical investigation of CarisolvTM on pulp tissue J. Dent, 2001, vol. 29, No. 4, pp. 275-281.
Peskin et al., Chlorine transfer between glycine, taurine, and histamine: reaction rates and impact on cellular reactivity; Free Radical Biology & Medicine, vol. 38, No. 3, pp. 397-405, (2004).
Thomas et al., Preparation and characterization of chloramines; Methods in Enzymology, vol. 132, pp. 569-585 (1986).

* cited by examiner

PREPARATION FOR TREATMENT OF A NON-ORAL TREATMENT SITE COMPRISING AN ACTIVE CHLORINE COMPOUND AND AMINO ACIDS

CROSS-REFERENCE TO RELATED APPLICATIONS

This application is a U.S. National Phase Application of International Application No. PCT/EP2013/064919, filed on Jul. 15, 2013, which claims priority to Swedish Patent Application No. 1250891-7, filed Jul. 24, 2012, each of which are hereby incorporated by reference in their entirety.

TECHNICAL FIELD

The present invention relates to a kit and a preparation for use in the prevention and/or treatment of sores, wounds, ulcers or the like, or a fistula or otitis. Furthermore, the invention also relates to a method of using the kit and preparation.

TECHNICAL BACKGROUND

Sores and wounds, such as chronic wounds, are common and cause patients to suffer and burdens to society in terms of costs (see Serens T, Bates-Jensen B, Carter M J, Cordrey R, Driver V, Fife C E, et al. *Consensus principles for wound care research obtained using Delphi process. Wound repair and regeneration.* 2012 May; 20(3):284-93).

Known methods for treating the sores and wounds include cleaning with water, for example. Antiseptics and antibiotics are also often used in the prevention and treatment of infections in, for example, skin sores or skin ulcers. Skin ulcers are sores wherein tissues disintegrate and may result in loss of epidermis, dermis and even subcutaneous tissue. A skin sore, in particular a skin ulcer, may be difficult to treat and may require long-term treatment. The treatment then includes reducing the risk of infections and inflammations as well as keeping an environment for the sore. The topical antiseptics and antibiotics have been used to at least reduce the risk of infections.

Chlorine compounds, such as hypochlorous acids and Chloroamine T have been studied for their capabilities as antiseptics. One problem with known compounds is that they may be aggressive and toxic to living tissues and that they often are unstable substances, thus leading undesired disintegration of the substances, and inactivation thereof, for example.

Antiseptic solutions with N-chlorotaurine has also been indicated for use in the treatment of infections and the controlling of inflammations (Waldemar Gottardi and Markus Nagl, N-chlorotaurine, a natural antiseptic with outstanding tolerability, J Antimicrob Chemother 2010; 65: 399-409). N-chlorotaurine is a N-chloro derivative of the sulfonic acid taurine. In said article, N-chlorotaurine is mentioned as a natural, long-lived oxidant that offers a compromise between sufficient microbicidial activity and tissue tolerability. Also indicated is the use of antiseptic solution including N-chlorotaurine for the treatment of infections in skin ulcers.

Although the prior art substances to some extent may alleviate the problems of preventing and treating skin sores, wounds, ulcers or the like, there is still a great need for improved and/or alternative substances or preparations that at least are interchangeable with known substances or preparations for said prevention or treatment.

SUMMARY

In view of known substances for use in treatment of skin wounds, for example, it is an object to provide an improved and/or alternative preparation with low toxicity and good stability, which preparation may be useful in the prevention or treatment of sores, wounds, ulcers or the like The object is wholly or partially achieved by a kit of parts according to appended claim 1, a treatment preparation according to appended claim 19, a use according to appended claim 24 and a method according to appended claim 29. Embodiments are set forth in the appended dependent claims and in the following description and examples.

According to one aspect, there is provided a kit of parts for use in prevention and/or treatment of sores, wounds, ulcers or the like, or a fistula or otitis. The kit of parts comprises
 a) a first aqueous component comprising one or more amino acids, and
 b) a second aqueous component comprising an active halogen compound.

The pH of the first component and/or the second component is about 9 to 11.5.

The term "active halogen compound" herein refers to a halogen in the form of an ion, gas, salt or hypohalogenite of a halogen.

The two components are intended to be mixed together and thereby forming a treatment preparation for use in the application on a treatment site such as an ulcer. The treatment preparation has shown to be useful in the treatment of sores, ulcers, wounds, burns, and fistulas, and also in cases of being chronic and having infections, necrosis. The treatment preparation has also been tested on a subject suffering from otitis, wherein treatment preparation was indicated as useful in the treatment of otitis (data not shown). Thus, the treatment preparation is then also expected to aid in the treatment of otitis. It has also been shown to be useful as antiseptic and in the prevention of infections or inflammations. The treatment preparation is effective for the treatment of different types of treatment sites, such as chronic sores, ulcers, bedsores, vasculitis sores, and diabetic ulcers that are chronic. The treatment preparation also provides means for decomposing parts in a sore or the like, The decomposed parts may, for example, be bacteria, pus, necrotic cells or scab present in a sore or the like.

The first component reduces the aggressiveness of the active halogen compound to living tissues. The treatment preparation formed from the two components comprises one or more amino acids that are useful in the use and provide less aggressive and toxic means for treating a sore or the like. The treatment with the treatment preparation utilizes the two liquid components which when combined to the treatment preparation and applied on a site of treatment leads to a chemical reaction which is believed to result in primary halogenated amines in the form of (primary) halogenated amino acids such as primary chloroamino acids. By primary chloroamino acids is intended amino acids in which the amine carries one chlorine atom. The treatment disclosed herein is believed to utilize this chemical reaction. As used herein, the chemical reaction resulting in primary halogenated amino acids is denominated the first reaction.

The uses of chloroamines as is known in the art rely on the use of reactions that are subsequent to the first reaction and in which the preparation should have a low pH, i.e. just below neutral pH such as pH about 6. These subsequent reactions result in dihalogenated amines, i.e. amines in which the nitrogen carry two chlorine atoms. The pH is then normally lower than a neutral pH, which is contrary to the present treatment with the treatment preparation disclosed herein wherein the pH is high and basic. Thus, known methods of using chloroamines as antiseptics do not make use of the first reaction at basic pH, and instead use reactions such as reactions for forming dichloroamines at acidic pH such as about pH 6.

It is believed that the high pH here provides means for the desired reaction resulting in primary halogenated amino acids to occur on the treatment site, while also providing pain relieve and minimal aggressiveness to living tissues.

The formed treatment preparation has shown to provide a treatment wherein the pain a subject experiences during and after the treatment is reduced or even removed. At least, the treatment preparation does not provide any additional pain to the subject.

Furthermore, the use of the treatment preparation provides a possibility of reducing malodors that often emanates from an infected sore, wound or ulcer.

The provision of a kit in two parts provides a way of keeping the components stable and reducing the risk of decomposing the contents thereof before applying a prepared treatment preparation to a subject. Furthermore, the provision of a kit provides means to control that the desired reaction occurs in the treatment site.

The components will after being mixed also have low impact on the environment, as the mixed components will decompose into salts, gases and water in nature. Attention is drawn to the fact the concentrations of halogen such as chlorine used in the components and treatment preparations are lower than the amounts of chlorine used in chlorination of water for purification thereof or in normal house hold bleach product containing chlorine.

According to an embodiment, said pH of the first and/or second component may be about 9 to 11, or about 9.5 to 11.5, or about 10 to 11.5, or about 10.5 to 11.5, or about 11 to 11.5, or about 9 to 10.5, or about 9.5 to 10.5.

The prevention and/or treatment may involve pain relieving effects. The treatment preparation has surprisingly shown to provide such effects.

The treatment preparation may as indicated above also have antibacterial effects. The bacteria against which the treatment preparation may be useful are *streptococcus* such as MRSA, *staphylococcus, pseudomonas, Actino mycetes* and *Escherichia coli* (*E. coli*), in particular Extended-spectrum beta-lactamase (ESBL) producing *E. coli*.

The treatment preparation has shown to be able to minimize any use of antibiotics, and in one embodiment there is no need of using antibiotics for treating an infected treatment site. There are even indications that the treatment with the treatment preparation is more effective without the use of antibiotics than with antibiotics.

According to an embodiment, said sores, ulcers, fistulas or otitis are chronic and involve inflammations, infections and/or necrosis.

The treatment preparation obtainable by mixing the components has been shown useful in uses described herein for such chronic sites, wherein other known treatments have been shown unsuccessful.

According to an embodiment, the use is a non-oral use.

As will be evident from the disclosures herein, the treatment preparation that is obtainable by mixing the first and second components have surprisingly been shown to be useful in the prevention and/or treatment of non-oral treatment sites, such as skin sores, wounds and ulcers. Examples of skin sores, wounds and ulcers are a diabetic foot sore, an infected sore on the occiput, an infected ulcer, and ulcer on the leg and/or feet, an amputation wound, and an infected burn. In addition, the treatment preparation may be used for treating fistulas such as anal fistulas and otitis.

According to an embodiment, the active halogen compound may be an active chlorine compound.

According to an embodiment, the active chlorine compound may be, $Cl_2$, chloride, hypochlorite, chlorite, chlorate, perchlorate and/or a hypochlorite compound.

The ion compounds may be in the form of sodium, calcium, lithium and/or potassium form, e.g. the hypochlorite compound may be sodium hypochlorite, calcium hypochlorite, lithium hypochlorite and/or potassium hypochlorite.

According to an embodiment, the amount of the active halogen compound in the second component may be 0.5-5, 0.5-3, or 1-2% (by weight).

If nothing else is mentioned, percentage by weight herein means to refer to the weight of a compound or the like relative the total amount of the mentioned component or the like comprising the compound.

A treatment with a treatment preparation with these concentrations is effective and a concentration of 1-2% (by weight) seems in particular effective without causing any adverse effects.

A used herein, amino acids are organic compounds made from amine (—$NH_2$) and carboxylic acid (—COOH) functional groups, along with a side-chain specific to each amino acid.

According to an embodiment, said one or more amino acids may be selected from the group consisting of alanine, arginine, asparagine, aspartic acid, glutamic acid, glutamine, isoleucine, leucine, lysine and/or valine.

These amino acids have been identified to be of the kind to form primary halogenated amino acids such as primary chloroamino acids. The pK values and/or properties of the side chains are such that the primary halogenated amino acids may be formed and uses thereof also cause low risk, if any, of adverse effects on a subject.

In particular the one or more amino acids may comprise or consist of glutamic acid, leucine and lysine.

These amino acids have been shown useful in the use herein.

According to an embodiment, the first component may comprise 0.1-1% (by weight) of said one or amino acids.

In an embodiment, the amino acid concentration in the first component may be 0.4-1.0% or 0.5-1% (by weight), or 0.4-0.8% or 0.5-0.8% (by weight). The amino acid composition may contain a mixture of amino acids mixed in a relation by weight between each amino acid of about 2:1 to 1:2, preferably about 1:1.

According to an embodiment, the two components are intended to be mixed in the volume ratios of 1:2 to 2:1, preferably about 1:1, thereby forming the treatment preparation for use in the application on a treatment site being a sore, wound, ulcer or the like, or a fistula or otitis. At room temperature (20 degrees Celsius) and 1 atm of pressure (101325 Pa), and within 30 seconds after the components have been mixed together, the treatment preparation has a pH of about 9 to 11.5, or about 9 to 11, or about 9.5 to 11.5, or about 10 to 11.5, or about 10.5 to 11.5, or about 11 to 11.5, or about 9 to 10.5, or about 9.5 to 10.5.

In this way there is provided a way of securing that the reaction forming the primary halogenated amino acids have the proper reaction condition to occur on the treatment site as discussed herein. Thus, the provision of a kit in two parts provides means to control that the desired reaction occurs on the treatment site.

The use may involve applying the treatment preparation before or during gas bubbles appear from the treatment preparation. If an active chlorine compound is used, a smell of chlorine also appears along with the bubble formation. In this way, the occurrence of the proper reaction is secured.

According to one embodiment, the first aqueous component may further comprise a gel substance.

The gel substance provides moist keeping means to keep a moist environment for the treatment site, and in particular the gel substance reduces evaporation from the aqueous treatment preparation prepared from the first and second components, when applied to the treatment site. Furthermore, the gel substance also provides a proper consistency to the treatment preparation prepared from the two components.

A treatment preparation provided with a gel substance and having the "high" basic pH provides the use for effective prevention or treatment as mentioned herein above, while providing low aggressiveness to a treatment site. It seems that the treatment preparation also does not cause any pain during and after the treatment, and may even reduce or remove any pain during and after the treatment.

The gel substance may comprises or be polyethylene glycol (PEG), and/or carboxymethyl cellulose and/or a polysaccharide substance or a salt thereof, such as sodium carboxymethyl cellulose (Na-CMC).

Such a substance provides said consistency and acts as a moist keeping substance preventing said evaporation from the treatment preparation and treatment site.

According to an embodiment, the first component may comprise 2-4% (by weight) gel substance.

According to an embodiment, the first component may further comprise $TiO_2$ and/or NaCl.

$TiO_7$ seems to speed up the healing process.

The adding of NaCl adds to the active chlorine compound content present in the first component and treatment preparation. NaCl also has an antibacterial effect as such.

The components may be the ones sold under the trademark Carisolv® and Perisolv® (RLS Global AB).

According to an embodiment, the kit of parts may further comprise a third component being a fat-like cream.

The fat-like cream may be Vaseline®, zinc ointment or the like. It is intended to be applied along the edges of sores, wounds and/or ulcers to which the treatment preparation later is applied. The use of the fat-like cream provides a way of enclosing, so that the treatment preparation subsequently applied to the treatment site such as a sore is in contact with the desired treatment site of a subject and also kept there during the treatment. Thus, the fat-like cream may secure that the fluid preparation is kept in the sore and not flow away from there and entering the skin area surrounding the sore.

According to one embodiment, the kit may further comprise a forth component being a protective preparation.

The protective preparation is intended to be applied in-between and after treatments with the inventive preparation so as to protect the treatment site as well as to stimulate healing in the treatment site such as a sore or wound.

The protective preparation may contain vitamin D to improve the immunological defense and the healing process as the vitamin D is expected and known to stimulate. Furthermore, the protective preparation may further contain vitamin A to provide means for Vitamin D to reach the site for improving immunological defense as is known in the art.

Thus, vitamin A and D may be used to allow to stimulate the immune system and to improve the healing process.

The protective preparation may be cream or gel. The protective preparation may be an alcogel or glycerol containing gel that is known to the skilled person in the art. Examples of such protective preparations are i) Mano+ (from the company RLS Global AB) with Vitamin D and optionally Vitamin A, and ii) Vitamin A containing gel or cream sold under the trade mark Aberela (from the company Janssen-Cilag AB) to which Vitamin D may be added.

The protective preparation is applied to the treatment site, i.e. a sore, wound, ulcer or the like, wherein the preparation covers the treatment site. An alcogel or the like will provide a protective layer formed after the alcohol has evaporated.

The protective preparation is applied after and in-between treatments with the treatment preparation of the two components, and preferably applied after one or more treatments have been performed, and when there is no or little infection present in the treatment site as well as when granulation tissue is visible and the surface of the treatment site such as sore is in level with the healthy tissue (e.g. skin) surrounding the treatment site.

According to one aspect, there is provided a treatment preparation for use in prevention and/or treatment of sores, wounds, ulcers or the like, or a fistula or otitis, wherein the treatment preparation is obtainable by mixing a first and a second component as described herein above in the volume ratios of 1:2 to 2:1, preferably in the volume ratio of about 1:1.

Such a treatment preparation has shown the desired effects in uses described herein above, for example.

According to an embodiment, said treatment preparation has a pH of about 9 to 11.5 within 30 seconds after the components have been mixed together (at room temperature and 1 atm of pressure (101325 Pa)). The pH may be about 9 to 11 or about 9 to 10.5, or about 9.5 to 10.5, or about 9.5 to 11.5, or about 10 to 11.5, or about 10.5 to 11.5, or about 11 to 11.5.

This provides the means for the proper reaction to occur on the treatment site, while providing all the above-mentioned advantages.

As mentioned above, the use of treatment preparation may involve applying the treatment preparation before or during gas bubbles appear from the treatment preparation. If an active chlorine compound is used, a smell of chlorine also appears along with the bubble formation. In this way, the occurrence of the proper reaction is secured.

According to embodiments, said prevention and/or treatment may involve pain relieving effects as well as that said sores, ulcers, fistulas or otitis are chronic and involves inflammations, infections and/or necrosis. Furthermore, the use may be a non-oral use.

According to one aspect, there is provided a use of a treatment preparation as described above in the manufacture of a medicament for the prevention and/or treatment of sores, wounds, ulcers or the like, or a fistula or otitis.

Embodiments of the use of the treatment preparation are mentioned above under the aspect of the treatment preparation for use in prevention and/or treatment of sores, wounds, ulcers or the like, or a fistula or otitis.

According to one aspect, there is provided a method for use in prevention and/or treatment of a treatment site being a sore, wound, ulcer or the like, or a fistula or otitis.

The method comprises
a) applying a treatment preparation as described above to the treatment site of a subject to be treated, the treatment preparation comprising a first component with one or more amino acids and a second component with an active halogen compound;

b) incubating the treatment preparation applied in step a) so as to allow the treatment preparation to act on the treatment site and/or to decompose parts present in the treatment site;

c) removing the treatment preparation and decomposed parts from the treatment site; and d) optionally, repeating the steps a to c.

According to an embodiment, the treatment preparation in step b) may be allowed to incubate so long as gas bubbles appear from the treatment preparation. If an active chlorine compound is used, a smell of chlorine also appears along with the bubble formation. Finally, the bubbles and chlorine smell disappear in the treatment preparation, wherein the incubation is stopped.

According to an embodiment, the treatment preparation in step b) may be incubated for about 30 s to 10 min, preferably for about 30 s to 5 minutes.

According to an embodiment, step c) may involve rinsing or cleaning the treatment site with water, saline or the like.

In most cases, water may be used, as NaCl will be present in the treatment site following step b).

A dry compress or pad, or a compress or pad wetted with water, saline or the like, may also be also be used to clean the treatment sites and remove any decomposes parts therein. Compresses or pads that comprise silica or a activated carbon may also be used for efficient cleaning and/or removal of excess fluids and decomposed parts. Compresses or pads may also be used to cover the treatment site in-between and after treatments with the inventive treatment preparations so as to provide a proper environment for healing.

According to an embodiment, step c) involves removing bacteria, pus, and/or necrotic parts.

A fat-like cream as discussed herein above may prior to step a) be applied along the edges of sores to which the treatment preparation is applied. This provides an enclosure of the portion or area to be treated, such as sore, so that the applied treatment preparation is in contact with the desired body portion of a subject and also kept there during the treatment. Thus, the fat-like cream may secure that the fluid preparation subsequently applied on a sore is kept in the sore and does not flow away from there and entering the skin area surrounding the sore According to an embodiment, the treatment site may in a step following step d) be covered with a protective preparation as described herein above.

The treatment preparation may shortly prior to step a) be prepared by mixing the first and second component, so as to allow a fresh treatment preparation and the proper treatment and reaction conditions as discussed above.

The method may involve applying the treatment preparation (step a) before or during gas bubbles appear from the treatment preparation. If an active chlorine compound is used, a smell of chlorine also appears along with the bubble formation. In this way, the occurrence of the proper reaction is secured.

According to one embodiment, the treatment preparation is prepared prior to step a), by mixing the first and second components and that step a) occurs within 2 minutes, more preferred within 1 minute, 45 seconds or 30 seconds, after the components have been mixed together.

According to embodiments, said prevention and/or treatment in the method may involve pain relieving effects as well as that said sores, ulcers, fistulas or otitis are chronic and involves inflammations, infections and/or necrosis. Furthermore, the use may be a non-oral use.

The invention will now be described in more detail with reference to embodiments, figures and examples.

DETAILED DESCRIPTION OF EMBODIMENTS

Figure 1:
FIG. 1 shows a photo of an ulcer before any treatment with the treatment preparation according to the invention.

Sores and wounds, such as chronic wounds and ulcers, are common and represent a considerable burden to patients in terms of suffering of pain and disability as well as a burden to society in terms of costs (Serens T, Bates-Jensen B, Carter M J, Cordrey R, Driver V, Fife C E, et al. *Consensus principles for wound care research obtained using Delphi process. Wound repair and regeneration.* 2012 May; 20(3): 284-93).

Known methods of treating chronic wounds and ulcers include cleaning with water or a solution such as saline several times a week and dressing the wound or ulcer in-between the cleanings with some sort of active, usually antimicrobial dressing such as Suprasorb®, silver, Aquacel®, iodide and Sorbact®.

The costs of the treatment cleaning are considerable and requires hours of work by nurses, for example. The effectiveness of treatment by both cleaning and dressing is measured in terms of healing, reduction in wound size and reduced pain, progressing of wound or ulcer, how often the wound and ulcer have to be cleaned, how long time the treatment takes in weeks and months, the need of using antibiotics. Few studies concerning treatment of wounds and ulcers reach an endpoint healing.

Inflammation is caused by local infection and/or damaged tissue. The typical signs of a local infection are pain, heat, swelling, redness and loss of function. However, in chronic wounds the patient often has comorbidities that suppress the sign of an inflammation. As a result, identifying infections in chronic wounds may be difficult and there is a need to rely on other signs and symptoms. Chronic wounds are, for example, diabetic foot ulcers, venous leg ulcers, arterial leg/foot ulcers and pressure ulcers. An infection may be localized by: a) a new, increased or altered pain, b) delayed or stalled healing, c) periwound oedema, d) bleeding or friable granulation tissue, e) distinctive malodor or change in odour, f) wound bed discoloration, g) increased, altered or purulent exudates, g) induration, h) pocketing or bridging. Furthermore, the spreading of an infection as for a localized chronic infection, may be identified by: i) wound breakdown, j) erythema extending from the wound edge, k) crepitus, warmth, induration of discoloration spreading into a periwound area, and/or l) malaise or non-specific deterioration in patient's general condition (see: *World Union of Wound Healing Societies (WUWHS) Principles of best practice. Wound infection in clinical practice. An international consensus.* London MEP Ltd 2008. Available from www.woundsinternational.com).

As mentioned herein above, antiseptics and antibiotics are also used in the treatment of sores and wounds, such as chronic wounds or ulcers. As also mentioned above, solutions with N-chlorotaurine have been indicated for use as antiseptics in the treatment of skin ulcers, for example (Waldemar Gottardi and Markus Nagl, N-chlorotaurine, a natural antiseptic with outstanding tolerability, J Antimicrob Chemother 2010; 65: 399-409).

In a review relating to ulcers, saline different compositions and substances, such as formulations of aloe vera, saline spray, silver chloride and decyl glucoside, were tested for their capability of treating ulcers. It was concluded that "there is little trial evidence to support the use of any particular wound cleansing solution or technique for pressure ulcers and the lack of evidence should be a concern for health care providers" (Moore Z, Cowman S. *A systematic review of wound cleansing for pressure ulcers. J Clin Nurs,* 2008 17(15):1963-72).

Accordingly, there has been a need for exploration of new preparations for the treatment of sore, wounds, ulcers or the like that provide the possibility of treating a numerous of sores, wounds and ulcers, while being kind to the body part such as skin with which the preparation is in contact and which preparation may reduce the burdens to patients and society as mentioned herein above.

The present invention relates to a new use of a treatment preparation and a kit for preparing the treatment preparation as well as a method of treatment that were found to be useful in the above mentioned aspects of overcoming said problems. The use and method are related to the treatment of a sore, wound, ulcer, fistula or otitis.

Method

In the following, the invention will be exemplified by a method for preventions and/or treatments of, for example, burns, chronic wounds and ulcers, and fistulas as well as otitis, with inflammations, infections, pus and/or necrosis. A fistula may be an anal fistula, which is an abnormal path extending from the rectum to the skin surface.

The method and the treatment preparation used therein provide pain relieving effects as well as antibacterial effects and may be useful for the prevention and/or treatment of sores, ulcers, fistulas or otitis that are chronic and involves inflammations, infections and/or necrosis, in particular in a non-oral use.

In general, the method comprises the steps of:
applying a treatment preparation as described herein to a treatment site, such as a sore, fistula, otitis or the like, the treatment preparation comprising a first component with one or more amino acids and a second component with an active halogen compound;
incubating the treatment preparation applied in the step above so as to allow the treatment preparation to act on the treatment site and to decompose parts present therein;
removing the treatment preparation and/or decomposed parts from the subject; and
optionally, repeating the steps above.

The method described herein is useful in the treatment of, for example, a skin wound or ulcer, wherein portions of bacteria, pus, necrotic cells and/or scab are present, wherein the portions can be removed reduced with the method.

As mentioned herein above the method is also providing means for pain relief as well as antibacterial effects, wherein the amount of bacteria such as *streptococcus, staphylococcus, pseudomonas, Actino mycetes* and *Escherichia coli* (*E. coli*), in particular Extended-spectrum beta-lactamase (ESBL) producing *E. coli* being multiresistent to antibiotics, can be reduced or removed in the treatment site.

Furthermore, the use of the treatment preparation provides means for reducing malodors that often emanates from an infected sore, wound or ulcer.

The treatment preparation has a pH of about 9 to 11.5 within 30 seconds after it has been prepared by mixing the first and second components together (at room temperature and 1 atm of pressure (101325 Pa)). This provides a "high" basic pH, also when applied to the sore or the like. At such a pH, the treatment preparation is effective in the uses described herein, while being less aggressive to living tissues than known treatment preparations. The treatment preparation even provides the pain control and reduction as described herein. Furthermore, the high pH also secures that the desired reaction forming halogenated amino acids such as primary chloroamino acids occurs in the treatment site, as is also described further herein.

According to embodiments, the pH of the treatment preparation is about 9 to 11, 9 to 10.5, or 9.5 to 10.5, or about 9.5 to 11.5, or about 10 to 11.5, or about 10.5 to 11.5, or about 11 to 11.5.

Accordingly, the treatment preparation may be obtained by mixing a first aqueous component comprising one or more amino acids and a second aqueous component comprising an active halogen compound.

The active halogen compound may be any of the compounds described herein above, e.g. a hypochlorite compound such as sodium hypochlorite that may be present in the second component in an amount of 0.5-5, 0.5-3 or 1-2% (by weight). The low amount of 0.5-3%, in particular 1-2%, has shown to be sufficient for the treatment purposes as described herein. The first component may comprise said one or more amino acids in an amount of 0.1-1% (by weight), or any other concentrations mentioned herein. The amino acids therein in may be present in a relation by weight of about 2:1 to 1:2 between each other, preferably 1:1. Both the first and second component may have a pH of about 9 to 11.5 as adjusted with NaOH, for example. In embodiments, the pH is about 9 to 11, 9 to 10.5, or 9.5 to 10.5, or about 9.5 to 11.5, or about 10 to 11.5, or about 10.5 to 11.5, or about 11 to 11.5.

The two components may be mixed in the volume ratios of 1:2 to 2:1, preferably about 1:1, thereby forming the treatment preparation to be applied on a treatment site such as a wound. Preferably, the two components are mixed just before applying the treatment preparation to the treatment site. This reduces the risk of decomposition of the active components in the treatment preparation so that the desired reaction forming the primary halogenated amino acids is occurring during the treatment by incubating the treatment preparation in the treatment site. Thus, there is provided a way of providing a treatment preparation that includes active components at the application of the treatment preparation. By mixing the component just before application, the pH of the prepared treatment preparation is as mentioned above, thereby securing the advantages thereof.

The treatment preparation may shortly prior to applying it be prepared by mixing the first and second component, so as to allow a fresh treatment preparation and the proper treatment and reaction conditions as discussed above.

The treatment preparation may involve applying the treatment preparation before or during gas bubbles appear from the treatment preparation. If an active chlorine compound is used, a smell of chlorine also appears along with the bubble formation. In this way, the occurrence of the proper reaction is secured.

According to one embodiment, the treatment preparation is prepared by mixing the first and second components and followed by applying the treatment preparation within 2 minutes, more preferred within 1 minute, 45 seconds or 30 seconds, after the components have been mixed together.

The first component may also comprise a gel substance in an amount of 2-4% by weight.

The gel substance may be PEG, and/or a carboxymethyl cellulose and/or a polysaccharide substance, or a salt thereof, such as sodium carboxymethyl cellulose (Na-CMC). In one embodiment, the gel substance may be a high viscosity carboxymethyl cellulose gel. High viscosity of carboxymethyl cellulose is defined as 800-1300 (mPas; room temperature). The gel substance may also be a medium viscosity of carboxymethyl cellulose is defined as 400-800 (mPas). The gel substance provides moist keeping means to keep a moist environment for the treatment site, wherein evaporation from the treatment preparation and treatment site is prevented. Furthermore, the gel substance also provides a proper consistency to the treatment preparation prepared from the two components.

Applying a treatment preparation having said pH and optionally a gel substance is expected to provide effects according to the uses described herein.

According to an embodiment, said one or more amino acids may be selected from the group consisting of alanine, arginine, asparagine, aspartic acid, glutamic acid, glutamine, isoleucine, leucine, lysine and/or valine.

These amino acids have been identified to be of the kind that would form primary halogenated amino acids. The pK values and/or properties of the side chains are such that the primary halogenated amino acids may be formed and uses thereof also cause low risk, if any, of adverse effects on a subject.

In particular the one or more amino acids may comprise or consist of glutamic acid, leucine and lysine, as these amino acids have been shown useful in the uses herein.

The second component may further comprise one or more of the following compounds sodium chloride, titanium oxide, EDTA and sodium hydroxide.

Thus, there is provided a fluid preparation that may be applied on treatment site, such as a sore, ulcer or the like, or in a fistula, such as an anal fistula. The treatment preparation may have a consistency of a fluid, preferably of a liquid gel that upon application has the capability of spreading by itself on the surface of a sore, ulcer or the like to completely cover the surface.

The treatment preparation may also be injected into a portion to be treated such as a fistula.

The components and preparations for use according to the invention may be one of the ones sold under the trademark Carisolv® and Perisolv® (RLS Global AB).

In Table 1 herein below, an example of the content of the two components as part of a kit for providing the treatment preparation is provided. The contents correspond in large to the components and preparations sold under the trademark Carisolv® and Perisolv®.

TABLE 1

Contents of component 1 and component 2 to be mixed with each other just before application on a treatment site of a subject. (water is present up to 100% by weight)

|  | Component 1 (% by weight) | Component 2 (% by weight) |
| --- | --- | --- |
| NaOCl, | — | ≤1-2 |
| Amino acids Lys, Glu and Leu | 0.4-0.8* | — |
| TiO$_2$ | 0/0.03-0.1 | — |
| NaCl | 0.3-0.6 | — |
| Na-CMC (high viscosity/medium viscosity) | 2-4 | — |

TABLE 1-continued

Contents of component 1 and component 2 to be mixed with each other just before application on a treatment site of a subject. (water is present up to 100% by weight)

|  | Component 1 (% by weight) | Component 2 (% by weight) |
| --- | --- | --- |
| NaOH | Added in an amount providing pH 10 ± 0.5. | Added in an amount providing pH 10 ± 0.5. |

*total amount of amino acids, the amino acids being present in a relation by weight of about 1:1:1.

The method is based on the use of an aqueous preparation for the prevention or treatment of treatment sites being sores, wounds, ulcers or the like, or of a fistula such as an anal fistula, or otitis.

The method comprises applying the treatment preparation on the treatment site, whereupon the treatment preparation is allowed to incubate for a certain time allowing, for example, decomposed parts such as necrotic cells to be removed in a subsequent step and providing a reduced risk of infection.

The application of the treatment preparation is preferably performed so that part or whole of a first reaction between the active halogen compound and said one or more amino acids forming primary halogenated amines such as chloroamino acids occurs at the treatment site. This is achieved by applying the treatment preparation shortly after the first and second components have been mixed with each other, i.e. within 2 minutes, preferably within 1 minute, or most preferred within a few seconds, such as within 5 to 10 seconds, after the two components have been mixed together. The treatment preparation would then at the time of being applied to a treatment site have basic pH, e.g. a pH value of about 9 to about 11.5. The high pH provides the condition for the first reaction to occur, while the treatment preparation also provides a pain-relieving effect.

The uses of chloroamines as is known in the art rely on the use of reactions that are subsequent to the first reaction and that the preparation should have a lower pH than according to the aspects and embodiments described herein. The pH is then normally lower than a neutral pH, which is contrary to the present treatment wherein the pH is basic. Thus, known methods of using chloroamines as antiseptics does not make use of the first reaction, and instead using reactions such as reaction for forming dichloroamines that occurs in a much later stage.

In an embodiment of applying the treatment preparation on the treatment site, the method may include applying a fatty cream or the like (fat-like cream) along the sore, wound or ulcer edges before the treatment preparation is applied. The use of the fatty cream secures that the fluid preparation subsequently applied in the in the sore, wound or ulcer is kept in the sore, wound or ulcer and thereby not flowing away from there and entering the skin area surrounding the sore, wound or ulcer.

The fatty cream may be Vaseline® or zinc ointment. Nevertheless, any fat-like cream known to the skilled person to provide a liquid barrier along a sore edge, for example, may be used.

The fluid treatment preparation prepared from the two components is applied on the treatment site, such as a sore or ulcer. As mentioned herein above, the treatment preparation may have a consistency of a fluid, preferably of a liquid gel that has the capability of spreading by itself on the surface of a sore, ulcer or the like to completely cover the surface, while not flowing away from the treatment area and while the moist function is provided. The fluid treatment preparation is prepared shortly before the application thereof, by mixing the mentioned two components.

The treatment preparation is then incubated for a period to allow the effects of preparation. The treatment preparation has shown to achieve an effect already after 30 s, thus the preparation should at least be incubated for 30 s before it is removed. Nevertheless, a better effect has been shown if the treatment preparation is incubated for some minutes, and according to one embodiment the treatment preparation is incubated for 5 to 10 minutes. According, to one embodiment, the incubation is allowed to proceed until small gas bubbles and a smell of chlorine appear (if an active chlorine compound is used) and then disappears, which normally occurs within 5 to 10 minutes, and in most cases within 5 minutes. The effective mentioned first reaction of the treatment preparation is therefore in most cases completed within 5 to 10 minutes.

For many years, chloroamines have been used in the concentrations mentioned herein above for treatment in the oral cavity and no indications of toxicological effects on humans have been reported in connection with this. Toxicological studies on the mucous membrane in the oral cavity have not shown any negative effects (King C D, Stoudt M S. *Toxicological evaluations of a chemical caries-removing agent. Preclinical report, National patent development corporation,* 1985; *Carisolv™ sensitizing potential in the guinea-pg: Magnusson & Klingman test (G.P.M.T.), Caroline Ruat, Chrysalis, Preclinical services-Europe. a2PU1478,* 1998; *Carisolv™-Single application dermal irritation study in rat, Chrysalis, N* 789/002-D-23, 1998; *Carisolv™-Test to evaluate irritation of the buccal mucosa in the guinea-pig, Chrysalis,* 789/001, 1998; *Silica Fumed Carisolv™ Acute Oral Toxicity Study in the Rat. OECD Guideline No.* 420, *Acute Oral Toxicity—Fixed Dose Method, Bollen L. S. ScanTox, Lab No* 43241, *Dk,* 2001; *Removing the necrosis (compress with water or the like and drying).*

Thus, no major toxicological effects in the uses described herein are expected, when using the preparations described herein in which primary halogenated amino acids are formed for the uses described herein.

After the treatment preparation has been incubated, it is removed by for example rinsing or wetting the treatment site with water or the like, and optionally by wiping the treated area with a wet and/or dry compress/dressing/pad or the like.

Compresses or pads that comprise silica, a superabsorbent or an activated carbon may also be used for efficient cleaning and/or removal of excess fluids and decomposed parts. Compresses or pads may also be used to cover the treatment site in-between treatments as described herein below.

The above mentioned procedure may be repeated one or more times, if need be thereof.

Following the treatment, the treatment site may be covered with a dry compress/dressing/pad with a smooth surface facing the sore for non-sticking thereto, thereby allowing healing. Compresses or pads that comprise silica, a superabsorbent or an activated carbon may also be used. A cover with a bandage or the like may also be applied, in particular in a case of varicose ulcer, for example.

The above mentioned procedure (treatment) may then be repeated, e.g. once a week for 1 to 3 times or more, as long as there is a need thereof.

In-between the treatments, a protective preparation may also be applied on the treatment site so as to allow a proper moist environment to the treatment site as well as to stimulate healing within the site of treatment.

The protective preparation may be cream or gel such as an alcogel. It may contain glycerol, cholesterol, paraffin, propyl and methyl parahydroxybenzoate, polyethylene glycol (PEG), Vaseline, glycerol stearate, Vitamin A, Vitamin D. The protective preparation may also be a preparation of alcohol anhydrous ≥99.5%, 2-propanol ≥99%, 1-butanol ≥99%, glycerin (Meets USP testing specification), acrylates/C10-13 poly (acrylic acid $M_n$ 130,000, 2-Amino-2-methyl-1-propanol 95%, lavender, and vitamin D (detremin, drops).

Examples of protective preparations available on the market are i) Mano+ (RLS Global AB) with Vitamin D and optionally Vitamin A, and ii) Vitamin A containing gel or cream sold under the trade mark Aberela (Janssen-Cilag) to which Vitamin D may be added.

Vitamin D is intended to improve the topical immunological defense as the vitamin D is expected and known to stimulate. Vitamin A is known to stimulate Vitamin D to penetrate into tissues and reach the site of stimulating the immunological defense in the body.

The protective preparation is applied to the treatment site, i.e. a sore, wound, ulcer or the like, wherein the preparation covers the treatment site. An alcogel or the like will provide a protective layer formed after the alcohol has evaporated.

The protective preparation is applied after and in-between treatments with the treatment preparation of the two components, and preferably applied after one or more treatments have been performed, and when there is no or little infection present in the treatment site as well as when granulation tissue is visible and the surface of the treatment site such as sore is in level with the surrounding healthy tissue.

It will be realized that the present invention is not limited to the embodiments described above and that may be illustrated in the examples; rather a person skilled in the art will recognize many alterations and modifications that can be performed within the frame of the scope of protection of the appended claims. For example, whereas a preferred use of the treatment preparation is directed to the treatment of sores or fistulas, the preparation may be used for purposes of preventing or treating otitis, for example.

Examples, Background Thereof and Description of Test Methods

As mentioned herein above, sores and wounds are common and represent a considerable burden to patients and society in terms. There are few, if any, preparations that are known and that efficiently could be used to heal a chronic sore, wound and ulcer.

The treatments are therefore taking long times as well as they many times never lead to complete healing. In some cases, amputations are the only alternative treatment.

Many different preparations have been tested in the past and as mentioned herein above, solutions with N-chlortaurine have been indicated for use as antiseptics in the treatment of skin ulcers, for example (Waldemar Gottardi and Markus Nagl, N-chlorotaurine, a natural antiseptic with outstanding tolerability, J Antimicrob Chemother 2010; 65: 399-409).

As mentioned above, the little trial evidence to support the use of any particular wound cleansing solution or technique for pressure ulcers and the lack of evidence should be of a concern for health care providers.

There is a need for exploration of new preparations for the treatment of sore or the like that provide the possibility of treating a numerous of sores, wounds and ulcers.

Therefore, the preparations of the present invention were investigated for treatments of burns, skin sores, wounds, ulcers and even fistulas. Surprisingly and as will be evident herein below, these preparations were demonstrated to be highly effective in said treatments, wherein, for example, sores, burns, ulcers and fistulas could be completely treated and removed from patients. Attention is drawn to the fact that some of the patients have been suffering from the sores, ulcers or fistulas for many years and had been under several treatments using known preparations, wherein the sores, ulcers or fistulas could not be removed and treated.

Furthermore, the treatments do not involve any pain and the preparation seems to have a pain-relieving effect. In fact, the example subjects reported reduction of pain both instantly as well as in between treatments.

Nevertheless, the mixture of components should not be applied to newly-established epidermal tissues after burn as this in an example seemed to cause a pain reaction (see example 7 herein below).

Preparation Used in the Examples

If nothing else is mentioned herein below, the treatment preparation used in the examples below was prepared just before application by mixing one volume of a component containing aqueous NaOCl in an amount of 1-2% (by weight) with one volume of a component containing amino acids lys+Glu+Leu (1:1:1 relation and 0.7-0.8% total amino content by weight), $TiO_2$ (0.04% by weight), NaCl (0.3-0.6% by weight), Na-CMC (medium viscosity; 3% by weight), and NaOH (added to adjust the pH to be 9.5-10.5 by weight). Medium viscosity of carboxymethyl cellulose is defined as 400-800 (mPas).

½ to 2 ml of each component was used and mixed in a ratio of 1:1 in the examples.

The final pH of the treatment preparation before application was 9.5 to 10.5.

The pH was measured by pH Fiveeasy FE20-basic (VWR International AB) with an attached electrode, pH LE 420 (VWR International AB). A calibrations curve was performed with standard buffers at 4, 7 and 10 for each batch at ambient temperature and pressure, respectively. Recommended samples volumes at 1 ml were tested in triplicates and adjusted with sodium hydroxide and/or hydrochloric acid to meet the components pH requirements (pH 9.5-10.5).

A preparation obtained from two components with alternative contents according to embodiments described herein above and having said pH is also expected to provide similar effects as the specified treatment preparation used in the examples. For example the active chlorine compound may also be $Ca(OCl)_2$ or KOCl and the one or more amino acids may be the ones as mentioned in the embodiments or aspects of the appended claims.

Procedure of Treatment and Result Evaluation

The method according to the invention utilizes two liquid components which when combined and applied on an area of treatment leads to a chemical reaction resulting in primary halogenated amino acids. The used components and mixtures are described herein above and below.

In the following, the general procedure used in the examples is described. Any specific details and deviating procedural steps are set forth under respective examples.

The components were mixed and the resulting mixture, i.e. the treatment preparation, was applied immediately (within seconds at the most one minute) to the treatment site, e.g. an ulcer. In this way there was provided that the mentioned chemical reaction forming halogenated amino acids occurs in contact with the treatment site. The resulting chemical reaction was allowed to proceed so as to separate dead tissue from healthy tissue as well as decomposing and/or destroying bacteria. The mixture in the form a solution was left within the treatment area, e.g. ulcer, for 5 minutes or less, wherein the reaction proceeds such that bubbles and a smell of chlorine appear and then disappear in the preparation. In some cases it was required that the solution was left for more than 5 minutes, but 9 minutes as the longest incubation time.

The treatment area was then rinsed with water. The dead tissue and pus could then be easily removed from the ulcer without the need to exert force. If necessary, the sore or the like was alternatively cleaned with a wetted pad. To keep the solution within the ulcer, a fatty cream was applied to the skin lining the ulcer, in case there was a need thereof, as in the case of a burn. If nothing else is mentioned herein below, the fatty cream was Vaseline®. The fatty cream could also be and was in some cases applied to protect sore edges in-between treatments.

After removing bacteria, pus and dead tissue, a newly prepared treatment preparation was applied again to the treatment site, e.g. an ulcer, and was left in the treatment site for 5 minutes or less to eradicate any bacteria. The solution was removed by rinsing with water and/or the use of a wetted pad. This treatment with the application of the treatment preparation twice to the treatment site and removal thereof with water and/or pad was repeated regularly, as long as there was a need thereof. The exact repeating schedule is set forth in each example. Thus, the procedure may include treatments to be repeated around once a week, initially more frequently to be able to remove all pus and dead tissue.

In between the treatment the ulcer was left without any active treatment allowing the tissue to heal without anything disturbing elements.

As mentioned herein above, the treatment site may after a treatment and in-between treatments be lined with a protective cream or gel, such as an alcogel.

In example 1 below, Mano+ (from RLS Global AB) containing Vitamin D was used in-between and after treatments as mentioned herein below. Mano+ is an alcogel with glycerol and was applied after several treatments has been carried out, when there was no or little infection present in the wound as well as when granulation tissue was visible and the surface of the wound was in level with the surrounding healthy tissue, i.e. the surround skin. The alcohol in the preparation was allowed to evaporate after application to from a protective layer.

Preferably, the treatment site should in-between treatments and after treatments be protected by just a sterile non-sticking surface dry pad and the pad held in place by gauze. In most examples, such dry pads were used.

Furthermore, no compression was applied, e.g. a well-sealed bandage, as this in tests seemed to lead to bacterial cultivation in the area covered with the bandage.

The treatment of sores, ulcers or fistulas was or may be evaluated on the basis of on one or more of:
  the size of the sore as measured by the use of a ruler or the like and a camera/image;
  red spot around the sore, measured as the distance in mm from the sore edge to the outer red spot edge;
  Presence of any signs of chronic sores or wounds with infections or inflammations as mentioned herein, e.g. the presence of pocketing;
  patient survey of experienced pain before, during and after the treatment, by the use of the known Visual Analog pain Scale (VAS), rating the pain from 1 to 10, wherein 8 is horrible pain, for example;
  tests of the presence of known bacteria in the sore (before and after the treatment by the use of cultivation, for example); and comparing images of a sore are, the images being taken before and after the treatment, and by comparing images, an inflammatory response due to an infection may, for example, be indicated.

Example 1—Treatment of a Sore on a Foot of a Patient Suffering from Disorders Such as Diabetes and Circulatory Disorder The subject was a 74 year old male with a long history of illness and alcohol abuse.

He has diabetes mellitus, which has been and is treated with tablets. He also has arteriosclerosis with reduced blood circulation. He has had strokes and a heart failure which is being treated with diuretics. He has been smoking forty cigarettes a day since he was a teenager. He has osteoporosis and has had several bone fractures.

Four years ago he was involved in a car accident, his left foot and lower leg were stuck and he had to pull himself out of the vehicle resulting in damaged circulation to his left lower leg.

During two years preceding the accident he had several erysipelas in his left lower leg. The last two years he has had an infected, hard to heal ulcer between his first and second toe on his left foot and whatever treatment he has been given the ulcer was not healed and had increased in size. He had enormous pain and was treated with high doses of painkillers, which included Morphine. High doses of antibiotics (Heracillin®, Meda AB, 750 mg 1×3, and Ciprofloxacin, HEXAL NS, 750 mg 1×3) were also administered for four months. For the past one and a half year he has reduced his consumption of alcohol significantly. He has kept a prompt diabetic diet. Due to arterial-insufficiency in the left leg, dilation of the artery in the left leg was performed in November 2011. The ulcer has been cleaned twice a week and treated with Sorbact® (Abigo Medical AB) in between the cleaning of the ulcer. The cultivation tests also showed that there were plentiful of two strains of *pseudomonas* bacteria, which had a high resistance to antibiotics.

As the patient was suffering from a diabetic arterial foot ulcer and no treatment has shown any signs of improvement to the ulcer, the patient was referred to an Orthopedic clinic for amputation in February 2012. He got an appointment six weeks later. Before the appointment at the Orthopedic Clinic, he was accepting to test whether or not treatments using the procedure and the treatment preparation as described herein above would lead to an improvement and help him in any way.

In FIG. 1, a photo of the ulcer is shown before any treatment with the treatment preparation. The ulcer was located in between the big toe and second toe and was around 2 to 3 cm in depth and had a volume of around 12 cubic centimeters. A grey dead tissue was included in the ulcer. Cultivation tests showed that two *pseudomonas* bacteria strains were present in high amounts in the ulcer, the strains being resistant to antibiotics.

The patient was then treated using the treatment preparation described herein above following a treatment procedure as described above, in which totally 13 treatments were carried out. Dates, comments and results of the treatments are set forth herein below.

From the results, it is evident that the ulcer was healed after thirteen treatments and that the patient experienced reduction in pain by and during the treatment with the component mixture as described herein above.

Figure 2:
FIG. 2 shows a photo of the ulcer in FIG. 1 after treatments with the treatment preparation according to the invention.

FIG. 2 is a photo showing the foot at the final treatment, wherein the ulcer is healed except the presence of excess skin tissue to be removed and a scar. After the final treatment the patient was recommended to regularly apply Vaseline® on the scar.

Example 1—Comments and Results

The First Treatment (2012-03-02, i.e. 2 Mar. 2012)
Ulcer Status:
Length: 39 mm
Width: 14 mm
Depth of ulcer prior to treatment: 23 mm
Depth of ulcer after treatment: 30 mm
Surface area: 562 mm3
Total ulcer volume prior to treatment: 12558 mm3
Total ulcer volume after treatment: 16380 mm3
Pain
Patient estimated pain prior to treatment (VAS Scale): 10/10
Patient estimated during treatment (VAS Scale): 8/10
Brief Description of Leg:
Entire lower leg had erythema and there was a strong malodor emanating from the leg.
Purulent exudates could also be observed. Pocketing underneath the skin surrounding the ulcer could be observed.
FIG. 1 shows the ulcer before the first treatment with the treatment preparation.
Results after First Treatment
It was possible to easily remove dead tissue without any need to exert force thereon. The chemical reaction had caused dead tissue to become detached from healthy tissue parts. Nevertheless, not all dead tissue and pus could be removed. After the treatment the volume of the ulcer was increased due to removal of the dead tissue parts.
The Second Treatment (2012-03-06)
Ulcer Status:
Length: 37 mm
Width: 12 mm
Depth of ulcer prior to treatment: 23 mm
Depth of ulcer after treatment: 26 mm
Surface area: 444 mm$^3$
Total ulcer volume prior to treatment: 10212 mm$^3$
Total ulcer volume after treatment: 11544 mm$^3$
Pain
Patient estimated pain prior to treat (VAS Scale): 8/10
Patient estimated during treatment (VAS Scale): 6/10
Brief Description of Leg:
Only the foot had still erythema. There was still a malodor, but less than before. The ulcer seemed to be full of dead tissues, but after the first application of the inventive preparation and removal of dead tissue, the depth did not increase as much as in the first treatment. The surface area was reduced and the reduction of the pain had remained in-between the treatments and the reduction of pain continued thereafter.
Result after the Second Treatment
The pain experienced by the subject was reduced and the ulcer was a little bit smaller.
There was less erythema and most of the pus and dead tissue could easily be removed.
After the second treatment, there was no malodor and less pocketing underneath the skin lining the ulcer than prior the treatment.
The Third Treatment (2012-03-14)
Ulcer Status:
Length: 36 mm
Width: 12 mm
Depth of ulcer prior to treatment: 23 mm
Depth of ulcer after treatment: 23 mm Surface area: 360 mm$^2$
Total ulcer volume prior to treatment: 8280 mm$^3$
Total ulcer volume after treatment: 8280 mm$^3$
Pain
Patient estimated pain before treatment (VAS Scale): 3/10
Patient estimated pain during treatment (VAS Scale): 0/10
Brief Description of Leg:
Erythema has been reduced to the border of the ulcer. Significantly less malodor was present and the amount of exudates was low.
Results Following Third Treatment
All dead tissue was removed and only a little bit of pus remained. Patient experienced no pain and was able to stop taking any painkiller. The depth of the ulcer did not increase in size any longer.
The Fourth Treatment (2012-03-21)
Status Ulcer
Length: 35 mm
Width: 10 mm
Depth of ulcer prior to treatment: 19 mm
Depth of ulcer after treatment: 19 mm
Surface area: 350 mm$^2$
Total ulcer volume prior to treatment: 6650 mm$^3$
Total ulcer volume after treatment: 6650 mm$^3$
Pain
Patient estimated pain before treatment (VAS Scale)
Patient experience 2/10 VAS
Patient estimated pain during treatment (VAS Scale)
Patient experience 0/10 VAS
Brief Description of Leg:
No erythema could be observed. There was very little malodor. The amount of exudates had also been reduced and less pocketing could be observed.
Results Following Fourth Treatment
Cultivation tests showed that prior to treatment there remained just one strain of the two *pseudomonas* bacteria strains initially observed before any treatment. Nevertheless, the amount of the pseudomonad bacteria prior to treatment was still high and following the treatment the number was significantly reduced but still there was the same resistance to antibiotics. The patient was capable of walking on his leg and foot. He no longer needed to take antibiotics. Only some pus remained after the treatment.
Fifth Treatment (2012-03-28)
Ulcer Status:
Length: 32 mm
Width: 10 mm
Depth of ulcer: 15 mm
Surface area: 288 mm$^2$
Total ulcer volume: 4320 mm$^3$
Pain
Patient estimated pain before treatment (VAS Scale): 1/10
Patient estimated pain during treatment (VAS Scale): 0/10
Brief Description of Leg:
There was no malodor produced by the ulcer. There was very little pocketing and no erythema.
Results Following Fifth Treatment
Significantly less exudation could be observed in the ulcer than previously. The dressing of the ulcer could now be changed from closely fitting paddings to loose airy dry sterile pads with non-sticking surface and the use of gauze.
Sixth Treatment (2012-04-04)
Ulcer Status:
Length 29 mm
Width 9 mm
Depth of ulcer: 13 mm
Surface area: 261 mm$^2$
Total ulcer volume: 3393 mm$^3$
Pain
Patient estimated pain before treatment (VAS Scale): 1/10
Patient estimated pain during treatment (VAS Scale): 0/10
Brief Description of Leg:
Very little pus was observed prior to applying the inventive preparation. There was no malodor and no observable pocketing. Low amounts of exudate were present.
Results Following Sixth Treatment
Following the treatment, the subject had an appointment at the Orthopedic clinic and it was decided to postpone the amputation of the lower leg.
Furthermore, orthopedists ordered that the subject should be treated twice a week.
Seventh Treatment (2012-04-13)
Ulcer Status:
Length 28 mm
Width 8 mm
Depth of ulcer: 8 mm
Surface area: 224 mm$^2$
Total ulcer volume: 3393 mm$^3$
Pain
Patient estimated pain before treatment (VAS Scale): 1/10
Patient estimated pain during treatment (VAS Scale): 0/10
Brief Description of Leg:
There was no erythema, no pocketing, no malodor, and low amounts of exudates.
Result of Seventh Treatment
The treatment was performed by a person that had not been involved before and did not take any photo of the ulcer and did not make any notes about the results. Therefore, reference is made to the eighth treatment.
Eighth Treatment (2012-04-16)
Ulcer Status:
Length 24 mm
Width 7 mm
Depth of ulcer: 8 mm
Surface area: 168 mm$^2$
Total ulcer volume: 1344 mm$^3$
Pain
Patient estimated pain before treatment (VAS Scale): 1/10
Patient estimated pain during treatment (VAS Scale): 0/10
Result after Eighth Treatment
The ulcer looked totally clean and a fresh red granulation tissue could be observed in the ulcer bottom.
Ninth Treatment (2012-04-19)
Ulcer Status:
Length 23 mm
Width 6 mm
Depth of ulcer: 7 mm
Surface area: 138 mm$^2$
Total ulcer volume: 966 mm$^3$
Pain
Patient estimated pain before treatment (VAS Scale): 0/10
Patient estimated pain during treatment (VAS Scale): 0/10
Brief Description of Leg:
Minimal growth of *Pseudomonas* Bacteria could be detected.
*Staphylococcus* Bacteria was beginning to grow to minimal amounts
Results Following Ninth Treatment
The ulcer was lined with Mano+ to protect the area around the ulcer. Because the ulcer looked very clean it was decided to treat the subject only once a week again, thus allowing the ulcer to heal without any disturbance.

Tenth Treatment (2012-04-25)
Ulcer Status:
Length 22 mm
Width 6 mm
Depth of Ulcer: 6 mm
Surface Area: 132 mm$^2$
Total Ulcer Volume: 792 mm$^3$
Pain
Patient estimated pain before and after treatment (VAS Scale): 0/10

Results Following Tenth Treatment
One little bit of dead tissue was removed without the need to exert any force thereon.

After the treatment, there was a continuing in lining of the ulcer with Mano+ containing vitamin D.

Eleventh Treatment (2012-05-03)
Ulcer Status:
Length 18 mm
Width 4 mm
Depth of ulcer: 4 mm
Surface area: 72 mm$^2$
Total ulcer volume: 216 mm$^3$
Pain
Patient estimated pain before and after treatment (VAS Scale): 0/10

Results Following Eleventh Treatment
The ulcer was small. After the treatment, there was a continuing to line the ulcer with Mano+ containing vitamin D.

Twelfth Treatment (2012-05-11)
Ulcer Status:
Length 12 mm
Width 3 mm
Depth of ulcer: 2 mm
Surface area: 36 mm$^2$
Total ulcer volume: 72 mm$^3$
Pain
Patient estimated pain before and after treatment (VAS Scale): 0/10

Results Following Twelfth Treatment
After the treatment, there was a continuing to line the ulcer with Mano+ containing vitamin D. The depth of the ulcer was minimal and the ulcer seemed ready to heal completely.

Final Treatment (2012-05-18)
Ulcer Status:
Healed
Pain
Patient estimated pain before and after treatment (VAS Scale) 0/10

Brief Description of Leg:
The ulcer was healed. FIG. 2 is a photo showing the foot at the final treatment, wherein the ulcer is healed, except the presence of excess skin tissue to be removed and a scar.

After applying the treatment preparation once, it was possible to able to scrape excess skin off from the area were where ulcer had been located.

Results Following Final Treatment
The ulcer was healed and it was recommended to keep using Vaseline on the scar.

Example 2—Treatment of an Infected Ulcer

The subject was an 86 year old female with osteoporosis and suffering from fracture and undernourishment with no appetite. She had fallen over in Mars 2011 and had injured the front of her lower right leg resulting in a wound on the leg. The wound then became infected and red, and caused pain. She therefore received antibiotics Heracillin® 750 mg 1×3, altogether 100 tablets. The wound was initially cleaned every day and later on twice a week.

The cleaning of the wound and the treatment with antibiotics did not improve the wound status, and as a matter of fact the wound just grew in size. The subject then refused to take any more antibiotics.

The wound was concluded to be an arterial lower leg ulcer that at this stage had been present for eight months, during which time period i) the pain experienced by the subject has increased, ii) there was more exudates from the ulcer and iii) the subject had increasing difficulties when stepping and walking on the leg.

The next alternative treatment was amputation. The subject requested other means of treatment and she was accepting and receiving test treatments using the procedure and treatment preparation as described herein above. She had a height of 134 cm and a weight of 41 kg The patient was then treated using the treatment preparation described herein above following a treatment procedure as described above, in which totally three treatments were carried out. Vaseline was used to line the sore edges during the treatment. Dry pads were also used to cover the ulcer between the treatments.

Dates, comments and results of the treatments are set forth herein below. After the third treatment, the wound was healed and the subject was in no need for further treatments. She turned up 2012-03-14 in another matter, wherein the healing of the ulcer was confirmed.

Example 2—Comments and Results

First Treatment (2011-11-10)
Wound Status
Length 65 mm
Width 35 mm
Depth of wound: 5 mm
Surface area: 2275 mm$^2$
Total ulcer volume: 11375 mm$^3$
Pain
Patient estimated pain prior to treat (VAS Scale): 9/10
Patient estimated during treatment (VAS Scale): 5/10

Brief Description of Leg
The whole lower right leg was in erythema. A strong malodor emanated from the ulcer. Bacterial cultivation showed the presence of *Staphylococcus* resistant to fenoximetylpenicillin and flukloxacillin.

Results Following Treatment
Most of the dead tissue and pus could be removed without the need to exert any force thereon and the subject did not experience any pain during the removal. No compression bandage was used. There was a reduction of the pain experienced after the treatment as compared to before the treatment.

The Second Treatment (2011-11-17)
Wound Status
Length 40 mm
Width 13 mm
Depth of ulcer: 2 mm
Surface area: 520 mm$^2$
Total ulcer volume: 1040 mm$^3$
Pain
Patient estimated pain prior to treat (VAS Scale): 3/10
Patient estimated during treatment (VAS Scale): 0/10

Brief Description of Leg

The erythema was restricted to an area around the wound. The subject's ability to walk using the right leg has returned. The observed amount of exudates had reduced and thee was less malodor.

Results Following Treatment

Depth of wound has been reduced to 2 mm, following the removal of pale yellow necrosis and pus. The wound had reduced considerably in size.

The Third Treatment (2011-12-01)

Wound Status

Length 37 mm

Width 10 mm

Depth of wound: No depth, in skin level

Surface area: 370 mm$^2$

Pain

Patient estimated pain prior and during to treatment (VAS Scale): 0/10

Patient did not experience any pain

Brief Description of Leg

There was no depth of the wound in skin level. Furthermore, there was no erythema, pus, necrosis and malodor.

Results Following Treatment

The wound was ready to heal

Final Remarks

Because the wound had healed the patient found no need to come to the clinic any longer. She later turned up (2012-03-14) in another matter and it could be observed that the wound looked healed.

Example 3—Treatment of an Infected Sore on the Occiput

The subject was an 80 year old healthy male and in no need of long-term medication. He had an operation for ingual hernia in July 2010. He had no postoperative infection in the wound. In October 2011 he had a skin infection in his right second toe after he had kicked his foot into a door. He was first treated with Heracillin® 750 mg 1×3 for ten days and the Kåvepenin® 1 g×3 for ten days.

On Nov. 4, 2011, he fell over resulting in a wound on the back of his head, the occiput. He was referred to the emergency clinic for a checkup. He had a superficial round wound with a diameter around 30 mm. On Nov. 10, 2011, the wound was cleaned with descutan and dressed with mepilex and aquacel. On Nov. 11, 2011 he was referred to the nearest hospital for CT (Computed Tomography) of the head, due to increasing headache. The CT result showed no intracranial hemorragia or any fracture. The physician found no need for cleaning the wound.

On Nov. 11, 2011, the wound was very painful to the subject and he turned up at clinic for test treatments using the procedure and the treatment preparation as described herein above.

At this stage, the patient was suffering from an infected open wound on the occiput, the wound being infected with streptococci and staphylococci as decided by a standard cultivation test. He was then treated with the treatment preparation mentioned above and in between the treatments he had no dressing on the wound, as the wound was in the back of his head surrounded by hair and it was impossible to have an active dressing fitted thereon.

The treatment procedure was following the general procedure as described herein above and included that the treatment preparation described herein above was applied on the scab present in the wound.

The treatment was repeated around once a week, and totally two times. The sore was healed completely after three weeks. Dates, comments and results of the treatments are set forth herein below.

Example 3—Comments and Results

First Treatment (2011-11-14)

Wound Description

The wound on the occiput was 50 mm in diameter with a thick scab of a brown and yellow coloration. The wound contained pus underneath the scab. The area around the wound had erythema and oedema.

Pain

Patient estimated pain (VAS Scale): 7/10

The treatment did not inflict any pain to the patient.

After the treatment was performed the patient did not suffer from any pain following the removal of pus and necrosis.

Second Treatment (2011-11-21)

Wound Description

The wound on the occiput was 35 mm in diameter with a thin scab being yellow in coloration and a small amount of yellow pus. Erythema and oedema had decreased.

Pain

Patient estimated pain (VAS Scale): 3/10

The treatment still did not inflict any pain to the subject; in fact it reduced the pain. The scab could easily be removed and most of the pus could also be removed Third Treatment (2011-11-28)

Wound Description

The wound on the occiput was 20 mm in diameter. There was no pus in the wound. No erythema and oedema could be observed. Patient was no longer suffering from any pain.

Pain

Patient estimated pain (VAS Scale): 0/10

Comments

The wound looked totally clean after the treatment and seemed ready to heal.

Final Remarks

No more treatment was performed.

The wound was examined 2011-12-02, and it was found to be dry with no signs of infection. The wound was completely healed 2011-12-14.

Example 4—Treatment of an Amputation Wound

The subject was a 72 year old male with diabetes that had been treated with both tablets and insulin. The subject also suffered from renal function failure, hypertension, heart failure due to previous myocardial infarct, and failing cognitive function because of previous cerebral infarct. He also has had lung tuberculosis.

In autumn 2011, the subject visited Eritrea and he was hospitalized there because of diabetic related disorders. A small wound on his left first toe could be observed. When returning home to Sweden there was a necrotic ulcer on his left first toe. The necrotic ulcer was then cleaned several times a week.

Percutaneous transluminal angioplasty (PTA) was performed in February 2012. The necrotic ulcer increased in size no matter what treatment and the subject was referred for amputation. A first amputation of the front part of the left foot was then performed. The wound following the amputation did not heal and the subject also had a pressure ulcer on the heel. It was decided to amputate the lower left leg, which amputation was carried out on Apr. 7, 2012. The new amputation wound did not heal and he was suffering from the wound causing severe pain. He was prescribed antibiotics Heracillin® 750 mg×3 (on May 24, 2012) but the treatment still did not improve his condition.

The subject was then undergoing test treatments using the treatment preparation described herein above following a treatment procedure as described above. So far, totally three treatments has been carried out.

Dates, comments and results of the treatments are set forth herein below. From the results it could be concluded that the necrotic ulcer now decreases in size and seems to be on the way to heal.

Example 4—Comments and Results

First Treatment (2012-05-28)
Ulcer Description
A dark brown scab covered 75% the ulcer area. Underneath the scab there was a yellow pus and necrotic tissue. There was also malodor and oedema as well as purulent exudates.
Length: 27 mm
Width: 15 mm
Depth: 5 mm
Area: 405 mm$^2$
Volume: 2025 mm$^3$ There was also a small ulcer medially observed Estimated pain was not done because of language difficulties.

The treatment preparation was applied twice and incubated for 5 minutes each time and part of the pus and necrotic tissue and thick scab could be removed. The ulcer was dressed with dry sterile non-sticking pad that was fixed with tape Bacteria cultivation showed the presence of *E. coli* ESBL (extended spectrum Beta-lactamas) producing resistance pattern to R: Cefotaxim, Ceftazidim, Tobramycin, Ciprofloxacin, Pipera/tazobactam, S: TrimSulfa, and Amikacin.

Second Treatment (2012-05-31)
The subject smiled and was very pleased because he had no longer any pain and he could sleep during night-time. He said he now felt healthy and happy.
Ulcer Description
The dark brown scab was only covering 1/3 of the ulcer area, and there was less pus and necrosis. Furthermore, the ulcer was not easily bleeding any longer. There was also less malodor and exudates.
Length: 24 mm
Width: 12 mm
Depth: 3 mm
Area: 228 mm$^2$
Volume: 864 mm$^3$ The patient reported no pain during treatment, but he said he could feel it working.

The small ulcer earlier observed medially was healed.

The treatment preparation was applied and incubated for 9 minutes and then rinsed away with water and pus and necrosis were removed. The treatment preparation was applied a second time and incubated for 6.5 minutes and then rinsed away with water. The ulcer was dressed with a sterile non-sticking pad that was fixed with tape.

Third Treatment (2012-06-04)
Patient was still very pleased with the treatment, because he had no pain.

Ulcer Description
There was no scab left, as well as there was no pus and dead tissue lining the lower bit of the ulcer observed. There was no malodor and less exudate.
Length: 20 mm
Width: 9 mm
Depth: 3 mm
Area: 180 mm$^2$
Volume: 540 mm$^3$ Patient reported no pain during the treatment.

The treatment preparation was applied twice, incubated for five minutes each time and rinsed away with water following the incubation. Some pus and necrosis could be removed without any pain. The ulcer was covered with dry non-sticking pads fixated with tapes.

Example 5—Treatment of an Anal Fistula

The subject was a 38 year old male who has been suffering from an anal fistula for several years. An anal fistula is an abnormal path extending from the rectum to the skin surface. Anal fistulas typically become infected by bacteria present in the rectum, which in turn also result in opening of the fistula. The treatment of the fistulas often involves surgical intervention combined with antibiotic therapy.

In the present case, the subject was treated with antibiotics and by surgical closing of the fistula. These treatments were unsuccessful and the anal fistula was still present after the treatment.

The subject was then undergoing test treatments using the treatment preparation as described herein above, wherein the preparation was injected into the fistula and allowed to be left there. Surprisingly, only one treatment seemed to be required, as the subject seven days following the treatment informed the care institution that the wound fistula was healed and there was no need for further treatments.

Example 6—Treatment of Infected Ulcers on the Lower Part of the Leg and the Feet The subject was 36 year old female diagnosed with an unknown rheumatic illness as well as inflammation in the vascular arteries. The subject had several spherical infected ulcers on both legs and feet, the ulcers varying between 20 mm-40 mm in diameter. She had the ulcers for more than 6 years The subject was previously treated with anti-rheumatic tablets being Sendoxan Furthermore, the ulcers had previously been cleaned twice a day at the Rheumatic Clinic, Sahlgrenska University Hospital, Gothenburg. Sorbact® (Abigo Medical AB) was used to clean the ulcers. However, the subject suffered from an intense amount of pain and the pus and necrosis remained after treatments and cleaning.

The subject was then undergoing test treatments using the using the treatment preparation described herein above in general following a treatment procedure as described above. Vaseline was also applied on the ulcer edges and the ulcers were covered with dry pads between the treatments. Totally three treatments was carried out. Comments and results are set forth herein below.

Example 6—Comments and Results

First Treatment
Inventive newly prepared treatment preparation was applied to the ulcers for 5 minutes, and this was followed by removing the pus and necrosis with the possibility of not causing any pain to the subject.

Pain

Pain Rating prior to treatment VAS: 8/10
Pain Rating following treatment VAS: 1/10

Second Treatment (7 Days Following the First Initial Treatment)

Ulcer Status:

The ulcer diameters have been reduced to 10 mm-20 mm. There were no signs of necrosis and small amounts of pus.

Following Second Treatment Application:

Inventive newly prepared treatment preparation was applied for 5 minutes, after which the pus was easily removed without inflicting any pain to the patient. The ulcers were rinsed with water and then a newly prepared preparation was applied for another 5 minutes to eliminate the possibilities of any bacterial infections. The ulcers then looked ready to heal.

Pain

Pain Rating prior to treatment VAS: 2/10
Pain Rating following treatment VAS: 0/10

Third Treatment (7 Days Following the Second Treatment)

Ulcer Status:

The ulcers were either completely healed or had a maximum diameter of 10 mm.

There were no signs of pus

Treatment

The treatment preparation was applied twice and incubated for 5 minutes each time to reduce any chance of bacterial infections.

Pain

Pain Rating prior to treatment VAS: 0/10
Pain Rating following treatment VAS: 0/10

Result

A week after the third treatment all ulcers were healed. Attention is drawn to the fact that these ulcers had been present for around six years, no matter what treatment had been given.

Example 7—Treatment of an Infected Burn

The subject had on its backside an infected burn with a size of 5.5×6.6 cm.

The subject was undergoing test treatments using the treatment preparation described herein above, in general following a treatment procedure as described above, except that the preparation was first applied on the burn and incubated for 3 minutes, followed by cleaning the burn with a pad and once again applying the preparation and allowing it to incubate for 2 minutes. The subject reported lowered experienced and the size of the burn was reduced to 3×4 cm three days after the treatment. New skin tissue could be seen and no pus was present. The treatment preparation was applied once again, but due to the pain experienced by the subject when the preparation was in contact with the newly formed skin tissue, the treatment was interrupted after 2 minutes. The burn was healed eight days following the treatment.

Example 8—Measurement of pH and Clorine Content of the Treatment Preparation at Different Times The treatment preparation was prepared as described above. The chlorine content and the pH of the preparation was measured at 1 minute, 5 minutes, 10 minutes, 15 minutes and 60 minutes after mixing of the components. The chlorine test used was Cl2 1.005999.00, spectroquant (Merck) and measured by a spectrophotometer (Shimadzu 160) at the wavelength of 557 nm, where the active chlorine was established in the aliquots of the mixed solution. pH was measured under inert atmosphere using a pH meter from Metler-Toledo and an electrode from Orion. The results are shown in the table below where min. stands for minute(s) and M stands for molar (i.e. mole per liter).

| Time (min.) | pH | Active chlorine content (M) |
| --- | --- | --- |
| 1 | 11.15 | 0.086 |
| 5 | 10.87 | 0.071 |
| 10 | 10.56 | 0.061 |
| 15 | 10.37 | 0.053 |
| 60 | 9.15 | 0.041 |

Example 9—Treatment of Liquid from an Abscess with the Treatment Preparation

Cotton applicators were soaked with the liquid in an abscess after which they were exposed to the treatment preparation as follows.

Cotton applicator No. 1 was not treated with the treatment preparation and was used as a reference.

Cotton applicator No. 2. The treatment preparation was prepared as described above and immediately applied (i.e. applied within one minute) to cotton applicator No. 2.

Cotton Applicator No. 3. The treatment preparation was prepared as described above and allowed to stand for 5 minutes after which it was applied to cotton applicator No. 3.

Cotton applicator No. 4. The treatment preparation was prepared as described above and allowed to stand for 15 minutes after which it was applied to cotton applicator No. 4.

All cotton applicators were sent to the laboratory Unilab for establishing the type and amount of bacteria. The bacterial analysis followed normal bacterial cell growth procedure in which bacteria cell colonies were grown on agar plates, identified and counted by numbers. The amount of bacteria was classified as rich, moderate or sparse. A rich amount of bacteria was defined as more than 50 colonies on the agar plate, identified and counted under a microscope. A moderate amount of bacteria was defined as from 10 to about 50 colonies per agar plate, identified and counted under a microscope. A sparse amount of bacteria was defined as less than 10 colonies on the agar plate, identified and counted under a microscope.

The results showed that the samples mainly contained the MRSA bacteria (i.e. methicillin-resistant *staphylococcus aureus*) in the abscess liquid. Cotton applicator No. 1 was found to contain a rich amount of MRSA bacteria. Cotton applicator No. 2 was found to contain a sparse amount of MRSA bacteria. Cotton applicator No. 4 was found to contain a moderate amount of MRSA bacteria. Cotton applicator No. 3 was found to contain an amount of MRSA bacteria lying between a sparse amount and a moderate amount.

It can be concluded that the treatment preparation has a bactericidal effect, and the bactericidal effect is significantly better for a freshly prepared treatment preparation than for a treatment preparation that has been allowed to stand for some time prior to use.

EXAMPLES

Concluding Remarks

The inventive treatment preparation described herein above has shown to be able to dissolve dead tissue and eradicate bacteria without damaging healthy tissue.

The wounds, ulcers and anal fistula in the examples above healed or were on the way to heal within weeks after the first treatment with the treatment preparation and it seems as the healing was faster without antibiotics. The healing period also seemed to be shortened, when the ulcers and wounds were dressed loosely with dry non-sticking pads rather than well sealed bandage. Wounds and ulcers with a well enclosed bandage thereon seems provide an environment for bacteria to cultivate (not shown).

For two subjects with infected ulcers and wounds that have been treated a long time with conventional treatments and the only remaining treatment was amputation, it has been clearly shown that the present inventive preparation and treatment method is effective. The wounds were healed or on the way to heal and the subjects reported major reductions in experienced pains.

The signs of that the local infection and spreading infection were reducing were: less pain, less oedema, less malodor, less exudates, less pocketing, less erythema and no malaise. This in turn indicated that the ulcers and wounds were healing.

It seems that the inventive preparation can be used to clean fistulas, ulcers and wounds from bacteria, dead tissue and pus. When the ulcer and wound is clean, it enables the immune system to further heal the fistulas, ulcers and wound, wherein treatment with the inventive preparation seems to enhance the healing process.

The invention claimed is:

1. A method of treating a non-oral treatment site, the method comprising the steps of:
    a) applying a treatment preparation to the non-oral treatment site of a subject, wherein the treatment preparation is produced by the process of mixing:
        1) a first aqueous component comprising one or more amino acids selected from the group consisting of alanine, arginine, asparagine, aspartic acid, glutamic acid, glutamine, isoleucine, leucine, lysine and valine, and
        2) a second aqueous component comprising an active chlorine compound, wherein the first aqueous component and the second aqueous component are mixed, wherein the pH of the first component and/or the second component is from about 9 to about 11.5; and
    b) incubating the treatment preparation applied in step a) so as to allow the treatment preparation to act on the treatment site and/or to decompose parts present in the treatment site, thereby treating the non-oral treatment site.

2. The method according to claim 1, wherein the method further comprises a step c) of removing the treatment preparation and decomposed parts from the non-oral treatment site.

3. The method according to claim 1, wherein the treatment preparation in step b) is incubated for about 30 s to 10 min.

4. The method according to claim 2, wherein step c) comprises rinsing or cleaning the non-oral treatment site.

5. A method according to claim 2, wherein steps a) to c) are repeated and a protective preparation comprising vitamin A and/or vitamin D is applied after step c) and before repeated step a) and/or after the last repetition of step c).

6. The method according to claim 1, wherein, the treatment preparation is applied within 2 minutes of the first aqueous component and second aqueous component being mixed together.

7. The method according to claim 1, wherein the non-oral treatment site comprises an inflammation, an infection, and/or necrosis.

8. The method according to claim 1, wherein the active chlorine compound is selected from the group consisting of $Cl_2$, hypochlorite, chlorate, perchlorate and a hypochlorite compound, or a combination thereof.

9. The method according to claim 1, wherein the active chlorine compound is selected from the group consisting of $Cl_2$, hypochlorite, and a hypochlorite compound, or a combination thereof.

10. The method according to claim 1, wherein the active chlorine compound is selected from the group consisting of hypochlorite and a hypochlorite compound, or a combination thereof.

11. The method according to claim 1, wherein the amount of the active chlorine compound in the second aqueous component is from 0.5% to 5% (by weight).

12. The method according to claim 1, wherein the amount of the active chlorine compound in the second aqueous component is from 1% to 2% (by weight).

13. The method according to claim 1, wherein the first aqueous component comprises from 0.1% to 1% (by weight) of said one or more amino acids.

14. The method according to claim 1, wherein the pH of the treatment preparation is from about 10.5 to about 11.5.

15. The method according to claim 1, wherein the first aqueous component comprises glutamic acid, leucine and lysine.

16. The method according to claim 1, wherein the first aqueous component further comprises a gel substance.

17. The method according to claim 16, wherein the first aqueous component further comprises from 2% to 4% (by weight) the gel substance.

18. The method according to claim 16, wherein the gel substance comprises polyethylene glycol (PEG), carboxymethyl cellulose, or a polysaccharide substance, or a salt thereof.

19. A method of treating a non-oral treatment site, the method comprising the steps of:
    a) applying a treatment preparation to the non-oral treatment site of a subject, wherein the treatment preparation is produced by the process of mixing:
        1) a first aqueous component comprising from 0.1% to 1% (by weight) of glutamic acid, leucine and lysine and from 2% to 4% (by weight) of sodium carboxymethyl cellulose, and
        2) a second aqueous component comprising from 1% to 2% (by weight) of sodium hypochlorite, wherein the first aqueous component and the second aqueous component are mixed, wherein the pH of the first component and/or the second component is from about 9 to about 11.5; and
    b) incubating the treatment preparation applied in step a) so as to allow the treatment preparation to act on the treatment site and/or to decompose parts present in the treatment site, thereby treating the non-oral treatment site.

20. The method according to claim 1, wherein the first aqueous component and/or the second aqueous component comprises $TiO_2$ or NaCl, or a combination thereof.

21. A method according to claim 1, wherein the first aqueous component and the second aqueous component are provided by a kit of parts, and the pH of the first aqueous component and/or the second aqueous component is from about 9 to about 11.5.

22. A method according to claim 19, wherein
a) the first aqueous component comprises from 0.4 wt % to 0.8 wt % of glutamic acid, leucine, and lysine in weight ratio of about 1:1:1 being the one or more amino acids; from 2 wt % to 4 wt % of sodium carboxymethyl cellulose; from 0.3 wt % to 0.6 wt % of sodium chloride; optionally from 0.03 wt % to 0.1 wt % of titanium dioxide, sodium hydroxide in an amount to provide for a pH of 10±0.5 of the first aqueous component, and water up to 100 wt %, and
b) the second aqueous component comprises from 1 wt % to 2 wt % of sodium hypochlorite being the active chlorine compound, sodium hydroxide in an amount to provide for a pH of 10±0.5 of the second aqueous component, and water up to 100 wt %.

23. A method of treating a non-oral treatment site, the method comprising the steps of:
a) applying a treatment preparation to the non-oral treatment site of a subject, wherein the treatment preparation is produced by the process of mixing:
1) a first aqueous component comprising one or more amino acids selected from the group consisting of alanine, arginine, asparagine, aspartic acid, glutamic acid, glutamine, isoleucine, leucine, lysine and valine, and
2) a second aqueous component comprising an active chlorine compound, wherein the first aqueous component and the second aqueous component are mixed in a volume ratio of about 1:2 to 2:1, wherein the pH of the first component and/or the second component is from about 9 to about 11.5; and
b) incubating the treatment preparation applied in step a) so as to allow the treatment preparation to act on the treatment site and/or to decompose parts present in the treatment site, thereby treating the non-oral treatment site.

24. A method according to claim 23, wherein the first aqueous component and the second aqueous component are mixed in a volume ratio of about 1:1.

25. A method according to claim 1, wherein the non-oral treatment site is a bedsore.

26. The method according to claim 1, wherein the non-oral treatment site is a wound.

27. The method according to claim 26, wherein the wound is an amputation wound.

28. The method according to claim 1, wherein the non-oral treatment site is an ulcer.

29. The method according to claim 28, wherein the ulcer is on the leg and/or feet.

30. The method according to claim 28, wherein the ulcer is a diabetic foot ulcer.

31. The method according to claim 19, wherein the non-oral treatment site is a sore, a wound, an ulcer, a fistula, or an otitis.

32. The method according to claim 23, wherein the non-oral treatment site is a sore, a wound, an ulcer, a fistula, or an otitis.

33. The method according to claim 23, wherein the non-oral treatment site is a bedsore, a wound, or an ulcer.

34. The method according to claim 1, wherein the non-oral treatment site is a sore.

35. The method according to claim 1, wherein the non-oral treatment site is a fistula.

36. The method according to claim 35, wherein the fistula is an anal fistula.

37. The method according to claim 1, wherein the non-oral treatment site is a burn.

38. The method according to claim 1, wherein the non-oral treatment site is an infected burn.

* * * * *